(12) United States Patent
Sakamoto et al.

(10) Patent No.: US 8,278,481 B2
(45) Date of Patent: Oct. 2, 2012

(54) METHOD FOR PRODUCING (METH)ACRYLIC ACID

(75) Inventors: Kazuhiko Sakamoto, Himeji (JP);
Naoki Serata, Himeji (JP); Toyofumi Sakai, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 324 days.

(21) Appl. No.: 12/451,701

(22) PCT Filed: May 15, 2008

(86) PCT No.: PCT/JP2008/058954
§ 371 (c)(1),
(2), (4) Date: Nov. 25, 2009

(87) PCT Pub. No.: WO2008/146613
PCT Pub. Date: Dec. 4, 2008

(65) Prior Publication Data
US 2010/0130778 A1      May 27, 2010

(30) Foreign Application Priority Data

May 29, 2007   (JP) ................................ 2007-141357

(51) Int. Cl.
*C07C 57/02* (2006.01)
(52) U.S. Cl. .......... 562/598; 562/512; 562/599; 562/600
(58) Field of Classification Search .................. None
See application file for complete search history.

(56) References Cited

U.S. PATENT DOCUMENTS

| | | | |
|---|---|---|---|
| 5,371,280 A | 12/1994 | Haramaki et al. | |
| 6,300,513 B2 | 10/2001 | Sakamoto et al. | |
| 6,599,397 B2 | 7/2003 | Sakamoto et al. | |
| 7,183,428 B2 | 2/2007 | Ueno et al. | |
| 7,288,169 B2 | 10/2007 | Yada et al. | |
| 7,332,624 B2 | 2/2008 | Nishimura et al. | |
| 7,473,338 B2 | 1/2009 | Yada et al. | |
| 2001/0005755 A1 | 6/2001 | Sakamoto et al. | |
| 2002/0002253 A1 | 1/2002 | Sakamoto et al. | |
| 2004/0015014 A1 | 1/2004 | Nishimura et al. | |
| 2004/0222077 A1* | 11/2004 | Yada et al. | 203/1 |
| 2004/0249199 A1 | 12/2004 | Ueno et al. | |
| 2005/0252760 A1 | 11/2005 | Yada et al. | |

FOREIGN PATENT DOCUMENTS

| | | |
|---|---|---|
| JP | 5-51403 | 3/1993 |
| JP | 2001-181252 | 7/2001 |
| JP | 2001-348359 | 12/2001 |
| JP | 2001-348360 | 12/2001 |
| JP | 2004-51489 | 2/2004 |
| JP | 2005-15478 | 1/2005 |
| JP | 2005-232007 | 9/2005 |

OTHER PUBLICATIONS

Saudi Arabian Notice of Substantive Examination Report (with English translation) issued Jan. 25, 2011 in corresponding Saudi Arabian Application No. 8290304.
International Search Report issued Jul. 1, 2008 in International (PCT) Application No. PCT/JP2008/058954.

* cited by examiner

*Primary Examiner* — Sudhakar Katakam
(74) *Attorney, Agent, or Firm* — Wenderoth, Lind & Ponack, L.L.P.

(57) ABSTRACT

The present invention provides a method for effectively preventing the precipitation related to manganese acetate in the pipe for sending a polymerization inhibitor and the like, and the polymerization of (meth)acrylic acid. A first method of the present invention for producing (meth)acrylic acid, characterized in comprising steps of: producing a (meth)acrylic acid-containing gas by catalytic vapor phase oxidation reaction; and obtaining a (meth)acrylic acid-containing fluid by providing the (meth)acrylic acid-containing gas into a condensation column or an absorption column; wherein manganese acetate is used as a polymerization inhibitor; manganese acetate is dissolved into a (meth)acrylic acid aqueous solution containing not more than 10% by mass of (meth)acrylic acid, and the like, to obtain a manganese acetate aqueous solution; and the manganese acetate aqueous solution is provided into the condensation column or the absorption column.

18 Claims, No Drawings

US 8,278,481 B2

METHOD FOR PRODUCING (METH)ACRYLIC ACID

TECHNICAL FIELD

The present invention relates to a method for producing (meth)acrylic acid.

BACKGROUND ART (Meth)acrylic acid is generally produced by providing (meth)acrylic acid-containing reactant gas produced by gas phase catalytic oxidation reaction into a condensation column or an absorption column to obtain a (meth)acrylic acid aqueous solution, and further purifying the solution. A method in which a (meth)acrylic acid aqueous solution is provided into an azeotropic separation column and azeotropicly distilled in the presence of an azeotropic agent has been widely known as one of such methods for purifying.

However, (meth)acrylic acid is polymerized very easily. Therefore, a polymerization inhibitor is added in a condensation column or an absorption column for inhibiting (meth) acrylic acid from being polymerized.

It is described in Japanese publication of unexamined patent application No. 2001-181252 that manganese acetate may be used as a polymerization inhibitor of (meth)acrylic acid together with an N-oxyl compound. An example in which manganese acetate is dissolved in a feedstock and fed to a distillation column is described in Japanese publication of unexamined patent application No. Hei 5-51403. The feedstock used in the publication is acrylic acid containing 30% by mass of water and 2.5% by mass of acetic acid. An example in which manganese acetate is dissolved in water with other polymerization inhibitors and fed to an azeotropic separation column is described in Japanese publication of unexamined patent application No. 2001-348359. In addition, it is described in Japanese publication of unexamined patent application No. 2004-51489 that a polymerization inhibitor is preferably fed with acrylic acid and manganese acetate is mentioned as one example of polymerization inhibitors.

DISCLOSURE OF THE INVENTION

The inventors of the present invention had studied a method for inhibiting the polymerization of (meth)acrylic acid in an azeotropic separation column, and obtained the following knowledge.

(1) First, manganese acetate was used as a polymerization inhibitor for (meth)acrylic acid, and an aqueous solution thereof was fed to an azeotropic separation column. As a result, a precipitate was generated in a pipe for transferring the manganese acetate aqueous solution to the azeotropic separation column, such as a liquid feed pump line. Further progress of such precipitation caused a trouble that the pipe was plugged to run short of the feed of the manganese acetate aqueous solution to the azeotropic separation column, and then a polymer of (meth)acrylic acid was generated in the azeotropic separation column. The precipitate in the pipe was originally conceived to be composed of manganese acetate itself, but subsequent studies had revealed that the precipitate was mainly composed of a modified product of manganese acetate.

(2) Next, manganese acetate was dissolved in a (meth) acrylic acid aqueous solution obtained by contacting a (meth) acrylic acid-containing gas with water or a product acrylic acid, and fed to the azeotropic separation column. As a result, the precipitate resulting from manganese acetate was restrained from generating, but yet (meth)acrylic acid was polymerized in the liquid feed pump line to cause plugging due to the polymer. In addition, the problem was that a polymer was generated in the azeotropic separation column and the polymer adhered to the inner surface of an apparatus.

The above-mentioned problems were similarly caused also in feeding manganese acetate to a condensation column or an absorption column.

Under the above-mentioned circumstances, an object of the present invention is to provide a method for effectively preventing the precipitate resulting from manganese acetate in a pipe and a purification column, and the polymerization of (meth)acrylic acid, as described above. For further details, in producing (meth)acrylic acid, the precipitation resulting from manganese acetate as a polymerization inhibitor in the pipe and the polymerization of (meth)acrylic acid are restrained in the purification process such as condensation and absorption of a (meth)acrylic acid-containing gas or azeotropic separation of (meth)acrylic acid.

The inventors of the present invention had earnestly studied for solving the above-mentioned problems. As a result, the inventors had completed the present invention by finding out that when manganese acetate as a polymerization inhibitor is dissolved in a (meth)acrylic acid aqueous solution of comparatively low concentration and the like and fed to an azeotropic separation column and the like, the precipitation resulting from manganese acetate and the polymerization of (meth) acrylic acid are hardly caused.

A first method of the present invention for producing (meth)acrylic acid is characterized in comprising steps of: producing a (meth)acrylic acid-containing gas by catalytic gas phase oxidation reaction; and obtaining a (meth)acrylic acid-containing fluid by providing the (meth)acrylic acid-containing gas into a condensation column or an absorption column; wherein manganese acetate is used as a polymerization inhibitor; manganese acetate is dissolved into (a) a (meth)acrylic acid aqueous solution containing not more than 10% by mass of (meth)acrylic acid, (b) an aqueous solution of an organic acid other than (meth)acrylic acid, or (c) a mixed aqueous solution containing not more than 10% by mass of (meth)acrylic acid and an other organic acid, to obtain a manganese acetate aqueous solution; and the manganese acetate aqueous solution is provided into the condensation column or the absorption column.

A second method of the present invention for producing (meth)acrylic acid is characterized in comprising steps of: producing a (meth)acrylic acid-containing gas by catalytic gas phase oxidation reaction; obtaining a (meth)acrylic acid-containing fluid by providing the (meth)acrylic acid-containing gas into a condensation column or an absorption column; and purifying (meth)acrylic acid by providing the (meth) acrylic acid-containing fluid into a distillation column and/or a crystallizer; wherein manganese acetate is used as a polymerization inhibitor; manganese acetate is dissolved into (a) a (meth)acrylic acid aqueous solution containing not more than 10% by mass of (meth)acrylic acid, (b) an aqueous solution of an organic acid other than (meth)acrylic acid, or (c) a mixed aqueous solution containing not more than 10% by mass of (meth)acrylic acid and an other organic acid, to obtain a manganese acetate aqueous solution; and the manganese acetate aqueous solution is provided into one or more selected from a group consisting of the condensation column, the absorption column and the distillation column.

A third method of the present invention for producing (meth)acrylic acid is characterized in comprising steps of: producing a (meth)acrylic acid-containing gas by catalytic gas phase oxidation reaction; obtaining a (meth)acrylic acid-containing fluid by providing the (meth)acrylic acid-containing gas into an absorption column; and purifying (meth) acrylic acid by providing the (meth)acrylic acid-containing fluid into an azeotropic separation column and azeotropicly distilling the (meth)acrylic acid-containing fluid in the presence of an azeotropic agent; wherein manganese acetate is used as a polymerization inhibitor; manganese acetate is dissolved into (a) a (meth)acrylic acid aqueous solution containing not more than 10% by mass of (meth)acrylic acid, (b) an aqueous solution of an organic acid other than (meth)acrylic acid, or (c) a mixed aqueous solution containing not more than 10% by mass of (meth)acrylic acid and an other organic acid, to obtain a manganese acetate aqueous solution; and the manganese acetate aqueous solution is provided into the absorption column and/or the azeotropic separation column.

In the method of the present invention, a (meth)acrylic acid-containing gas is first produced by catalytic gas phase oxidation reaction. The reaction is well known to those skilled in the art, and it is possible for those skilled in the art to produce the (meth)acrylic acid-containing gas by the reaction in accordance with an ordinary method. For example, propylene, propane, acrolein or the like is used as a raw material compound, and a molecular oxygen-containing gas such as air is reacted with the compound in the presence of an oxidation catalyst. As a result of the reaction, a gas containing (meth)acrylic acid as a desired compound as well as water and acetic acid as a by-product is obtained.

Next, a (meth)acrylic acid-containing fluid is obtained by providing the obtained (meth)acrylic acid-containing gas into a condensation column or an absorption column. With regard to the operating conditions of the condensation column or the absorption column, conventionally known conditions may be applied.

The condensation column is a column in which the (meth) acrylic acid-containing gas is condensed to thereby separate a non-condensing gas and obtain a process fluid containing (meth)acrylic acid.

In the absorption column, the (meth)acrylic acid-containing fluid is obtained by contacting the (meth)acrylic acid-containing gas with an absorption fluid. Examples of such an absorption fluid include water, an organic solvent, a waste fluid of the (meth)acrylic acid production process and crude (meth)acrylic acid during purifying.

More specifically, the absorption conditions in the case of using the absorption column and using water as the absorption fluid are as follows:

Overhead temperature: 40° C. or more, 80° C. or less
Bottom temperature: 50° C. or more, 100° C. or less
Overhead pressure of the absorption column: 0 kPa or more, 30 kPa or less as gage pressure The overhead temperature of the absorption column lower than 40° C. may raise a possibility of increasing equipment costs and utilities costs for cooling. Also, the mixing amount of a substance having a boiling point lower than that of (meth)acrylic acid may be increased to cause a decrease in (meth)acrylic acid concentration in the (meth)acrylic acid-containing fluid and the waste water amount may be occasionally increased. On the other hand, the overhead temperature higher than 80° C. may raise a possibility of decreasing absorption efficiency of (meth)acrylic acid. The bottom temperature of the absorption column higher than 100° C. may possibly result in a case where the polymer production amount at the bottom is increased. The overhead pressure of the absorption column lower than 0 kPa (gage pressure) requires a decompression device. On the other hand, the pressure higher than 30 kPa (gage pressure) may occasionally result in a necessity of upsizing a blower for feeding a source gas to a catalytic gas phase oxidation reactor.

(Meth) acrylic acid is purified from the obtained (meth) acrylic acid by using an azeotropic separation column, a distillation column, a crystallizer or the like. Needless to say, (meth)acrylic acid may be purified by combining two or more of these. With regard to the specific operating conditions of these purifying means, conventionally known conditions may be applied.

In particular, when (meth)acrylic acid is absorbed by waste water or the like with the use of the absorption column, comparatively much water is contained in the obtained (meth) acrylic acid-containing fluid, so that (meth)acrylic acid is preferably purified by azeotropic distillation.

The operating conditions of the azeotropic separation column are not particularly limited, and the conditions generally used can be applied as described above. Specifically, for example, the following conditions can be applied: an overhead temperature of 35° C. or more and 50° C. or less, a bottom temperature of 80° C. or more and 110° C. or less, a overhead pressure of 10 kPa or more and 40 kPa or less (absolute pressure), and a reflux ratio of 0.3 or more and 2.0 or less. The overhead temperature of the azeotropic separation column lower than 35° C. requires equipment costs and utilities costs for cooling. On the other hand, the temperature higher than 50° C. may possibly result in a case where the polymer production amount is increased. The bottom temperature of the azeotropic separation column higher than 110° C. may raise a possibility of increasing the polymer production amount at the bottom. Examples of an azeotropic agent include toluene.

The operating conditions of the distillation column also are not particularly limited, and the conditions generally used can be applied. For example, the boiling point of acrylic acid and the boiling point of methacrylic acid at normal pressure are respectively 139° C. and 163° C., so that the overhead temperature can be determined as approximately 40° C. or more and 90° C. or less, and the overhead pressure can be determined as approximately 1 kPa or more and 40 kPa or less as absolute pressure.

With regard also to the crystallizer, conventionally known crystallizers can be used. For example, either a continuous crystallizer or a batch crystallizer may be used, and crystallization can be performed in one stage, or two stages or more.

In the present invention, manganese acetate is used as a polymerization inhibitor. Manganese acetate has been conventionally dissolved in water or crude (meth)acrylic acid during purifying, and then fed to each purification column. However, the problem is that the precipitate derived from manganese acetate such as a modified product of manganese acetate is caused in a pipe for feeding, or a polymer of (meth) acrylic acid is produced. Therefore, in the present invention, manganese acetate is dissolved into (a) a (meth)acrylic acid aqueous solution containing not more than 10% by mass of (meth)acrylic acid, (b) an aqueous solution of an organic acid other than (meth)acrylic acid, or (c) a mixed aqueous solution containing not more than 10% by mass of (meth)acrylic acid and an other organic acid, to obtain a manganese acetate aqueous solution, and the solution is provided into one or more of the above-mentioned condensation column, absorption column, azeotropic separation column and distillation column. The coexistence of manganese acetate with an appropriate amount of (meth)acrylic acid or an other organic acid can restrain the above-mentioned precipitate and polymer from being generated, and the production of (meth) acrylic acid over a long period can be stably performed.

Examples of the above-mentioned mother liquor (a) include the following:

(1) (Meth) acrylic acid aqueous solution of which concentration is adjusted to not more than 10% by mass by adding water to crude (meth)acrylic acid or purified (meth)acrylic acid obtained through the purification process (2) (Meth)acrylic acid aqueous solution of which concentration is adjusted to not more than 10% by mass by adding water to (meth)acrylic acid solution obtained from the condensation column or the absorption column The concentration of (meth)acrylic acid in the above-mentioned mother liquor (a) is preferably not less than 0.1% by mass. When the concentration is not less than 0.1% by mass, the precipitation resulting from manganese acetate can be restrained more certainly. On the other hand, when the concentration is more than 10% by mass, a possibility of producing a polymer of (meth)acrylic acid may raise. The concentration is more preferably not more than 5%.

Other impurities may be contained in the above-mentioned mother liquor (a) as long as the effect of inhibiting polymerization is not deteriorated. Examples of the impurities include a by-product derived from catalytic gas phase oxidation reaction and a by-product produced in each purification process.

Examples of the above-mentioned mother liquor (b) include the following:

(1) Acetic acid aqueous solution obtained by dissolving industrial acetic acid in water (2) Waste water containing formic acid, acetic acid, propionic acid, maleic acid, (meth)acrylic acid dimer or the like obtained in the production process of (meth)acrylic acid, i.e. process waste water (3) Waste water of which concentration is properly adjusted by adding water to the above-mentioned process waste water The concentration of the organic acid other than (meth) acrylic acid in the mother liquor (b) is preferably not less than 0.1% by mass and not more than 20% by mass. When the concentration is not less than 0.1% by mass, pH of the manganese acetate aqueous solution can be rendered sufficiently acidic. Meanwhile, when the concentration is more than 20% by mass, a possibility of excessively increasing the cost of removing these organic acids may raise.

Formic acid, acetic acid, propionic acid, maleic acid and (meth)acrylic acid dimer are by-produced in the production process of (meth)acrylic acid. Therefore, process waste water containing at least one kind of formic acid, acetic acid, propionic acid, maleic acid and (meth)acrylic acid dimer obtained in the production process of (meth)acrylic acid is preferably utilized as the mother liquor (b) in view of the costs.

Examples of the above-mentioned mother liquor (c) include an aqueous solution of which concentration is adjusted to not more than 10% by mass by adding water to the process waste water containing (meth)acrylic acid, formic acid, acetic acid, propionic acid, maleic acid or (meth)acrylic acid dimer, obtained in the production process of (meth) acrylic acid. The (meth)acrylic acid concentration is more preferably adjusted to not less than 0.1% by mass and not more than 5% by mass. The concentration of the organic acid other than (meth)acrylic acid in the mother liquor (c) is not particularly limited, process waste water can be used directly or by properly adding water, and the concentration is more preferably not less than 0.1% by mass and not more than 20% by mass.

The concentration of manganese acetate in the manganese acetate aqueous solution may be properly adjusted and yet is preferably not less than 0.1% by mass and not more than 30% by mass. When the concentration is less than 0.1% by mass, for example, the amount of water to be provided may be occasionally increased in the case of providing the aqueous solution into the azeotropic distillation column to raise the costs necessary for separation thereof. Also, a large amount of water may raise a possibility to promote the polymerization of (meth)acrylic acid. On the other hand, the concentration of more than 30% by mass may possibly raise a possibility that the impurities contained in manganese acetate aqueous solution promote side reaction and polymerization. The concentration is more preferably not less than 0.5% by mass and not more than 20% by mass.

The pH of the above-mentioned manganese acetate aqueous solution is preferably adjusted to a range of not less than 1 and not more than 4. The pH of more than 4 may possibly raise a possibility of generating the precipitate resulting from manganese acetate. On the other hand, the pH of less than 1 may possibly result in a case where an excessive amount of acid is required. The pH can be adjusted by the concentration of (meth)acrylic acid and the other organic acid in the above-mentioned mother liquor.

A polymerization inhibitor known as being effective in inhibiting polymerization of (meth)acrylic acid may be used as required together with manganese acetate. Examples of these polymerization inhibitors include phenolic compounds such as hydroquinone and p-methoxyphenol; amine compounds such as phenothiazine; copper salt compounds such as copper dibutyl dithiocarbamate; and N-oxyl compounds such as 2,2,6,6-tetramethylpiperidinooxyl. In addition, the use of molecular oxygen in combination can improve the effect of inhibiting polymerization. The used amount of the polymerization inhibitors other than manganese acetate can be properly determined as long as the sufficient effect of inhibiting polymerization can be obtained.

Manganese (II) acetate and manganese (II) acetate tetrahydrate are commercially available as manganese acetate mainly, and either of them can be used in the present invention.

In the present invention, the above-mentioned manganese acetate aqueous solution is fed to one or more of the condensation column, the absorption column, the distillation column and the azeotropic separation column. In particular, the feeding of the above-mentioned manganese acetate aqueous solution to the condensation column or the absorption column allows more favorable production. In case where the generation of a polymer is restricted in the initial stage of the production process, the problems such that the polymer is accumulated in the periphery of later purification columns and a strainer and that the polymer is mixed into a product can be minimized.

A feeding method of the above-mentioned manganese acetate aqueous solution is not particularly limited, and yet the manganese acetate aqueous solution is preferably fed through a special pipe such as a liquid feed pump line so as not to be mixed with a process fluid.

The pipe for feeding the above-mentioned manganese acetate aqueous solution and a solution of other polymerization inhibitors may be selected in accordance with the feed amount of the manganese acetate aqueous solution or the like, and a comparatively thin pipe having a cross-sectional area of not less than 1 cm$^2$ and not more than 20 cm$^2$ is typically used. Therefore, the pipe has tended to be conventionally plugged by the precipitate derived from manganese acetate or the polymer of (meth)acrylic acid. In the present invention, however, such a problem can be solved by blending an appropriate amount of (meth)acrylic acid and the like with the manganese acetate aqueous solution.

The feed amount of the above-mentioned manganese acetate aqueous solution may be properly adjusted in accordance with the kind and scale of the equipment to be fed with the solution. For example, in the case of feeding the above-mentioned manganese acetate aqueous solution to the azeotropic separation column, the manganese acetate aqueous solution may be fed so that the amount of manganese acetate to the vaporized steam amount of (meth)acrylic acid in the azeotropic separation column becomes not less than 1 ppm and not more than 100 ppm. Also, the feed rate of the manganese acetate aqueous solution may be properly determined in a range of 1 cm/s or more and 50 cm/s less, for example.

The above-mentioned manganese acetate aqueous solution is fed to the inner wall of the purification column uniformly so that the polymerization of (meth)acrylic acid can be favorably restrained, and accordingly, the solution is preferably fed from a plurality of places.

EXAMPLES

The present invention is hereinafter described by referring to examples and comparative examples, but the present invention is not restricted thereto.

Example 1

Propylene was subject to catalytic gas phase oxidation by a molecular oxygen-containing gas to thereby obtain an acrylic acid-containing gas. The gas was provided into an acrylic acid absorption column and contacted with water to thereby obtain an acrylic acid-containing fluid. The acrylic acid-containing fluid was provided into an acrolein stripping column to strip acrolein and obtain an acrylic acid aqueous solution containing 65% by mass of acrylic acid, 30% by mass of water and 3.0% by mass of acetic acid. This acrylic acid aqueous solution was azeotropicly distilled by using toluene as an azeotropic agent, and using an azeotropic separation column provided with a sieve tray having a tray number of 60 and a tray spacing of 147 mm and provided with a distillation pipe at the overhead, a raw material feed pipe at the middle and a bottom fluid extraction pipe at the bottom.

The operating state during steady operation in the azeotropic separation column was an overhead temperature of 47° C.; a bottom temperature of 99° C.; an overhead pressure of 100 mmHg; a reflux ratio, i.e. the total number of moles of the reflux fluid per unit hour/the total number of moles of the distillatory fluid per unit hour, of 1.35; and a feed amount of the above-mentioned acrylic acid aqueous solution as a raw material fluid of 7.62 L/hour.

The distillate obtained from the overhead of the azeotropic separation column was provided into a tank, separated into an organic phase with toluene as the main component and an aqueous phase, and the organic phase was recycled as the reflux fluid into the azeotropic separation column.

Manganese acetate, copper dibutyl dithiocarbamate, hydronone, phenothiazine and molecular oxygen were used as polymerization inhibitors, and manganese acetate, copper dibutyl dithiocarbamate, hydronone and phenothiazine were provided from the overhead of the azeotropic separation column, while molecular oxygen was provided from the bottom into the azeotropic separation column. The used amounts of manganese acetate, copper dibutyl dithiocarbamate, hydronone and phenothiazine were respectively 50 ppm, 50 ppm, 100 ppm and 100 ppm with respect to the vaporized steam amount of acrylic acid. The molecular oxygen amount was 0.3% by volume with respect to the vaporized steam amount of acrylic acid. Copper dibutyl dithiocarbamate, hydronone and phenothiazine were provided into the azeotropic separation column by using a liquid feed pump exclusive to each of them.

With regard to manganese acetate, 2% by mass-acrylic acid aqueous solution produced by mixing 98 parts by mass of water and 2 parts by mass of product acrylic acid was used as a mother liquor, manganese acetate was dissolved into the mother liquor so that the manganese acetate concentration became 10% by mass, and thereafter the solution was provided into the azeotropic separation column. The pH of the 2% by mass-acrylic acid aqueous solution was 2.4.

The composition of the bottom extraction fluid in steady state was 97.0% by mass of acrylic acid, 0.03% by mass of acetic acid and 2.96% by mass of others. When continuous operation was performed under these conditions for two months, a stable state was constantly obtained. As a result of inspecting the inside of the azeotropic separation column after stopping the operation, generation of a polymer was scarcely confirmed.

The pH and the like of the used manganese acetate aqueous solution are collectively shown in Table 1.

Comparative Example 1

The azeotropic distillation of acrylic acid was performed in a similar manner to Example 1 except that manganese acetate was dissolved in water to obtain a manganese acetate aqueous solution having a concentration of 10% by mass and the solution was provided into the azeotropic separation column.

When continuous operation was performed under the above-mentioned conditions, plugging due to the precipitate was caused in the liquid feed pump line exclusive to the manganese acetate aqueous solution to result in a state where the predetermined amount of the manganese acetate aqueous solution could not be fed. When the operation was stopped 48 days after starting the operation to inspect the inside of the azeotropic separation column, a large amount of a polymer was produced therein.

Thus, it was found that the precipitate was generated when water was used as a mother liquor to dissolve manganese acetate and the solution was fed as a manganese acetate aqueous solution. The pH and the like of the manganese acetate aqueous solution are collectively shown in Table 1.

Comparative Example 2

An acrylic acid aqueous solution containing 65% by mass of acrylic acid, 30% by mass of water and 3.0% by mass of acetic acid as a raw material to be provided into the azeotropic separation column was used as a mother liquor, and manganese acetate was dissolved into the mother liquor so that the concentration became 10% by mass to prepare a 10% by mass-manganese acetate aqueous solution. The acrylic acid was azeotropicly distilled in a similar manner to Example 1 except for providing the manganese acetate aqueous solution into the azeotropic separation column.

When continuous operation was performed under the above-mentioned conditions, plugging due to a polymer was caused in the liquid feed pump line exclusive to the manganese acetate aqueous solution to result in a state where the predetermined amount of the manganese acetate aqueous solution could not be fed. When the operation was stopped 32 days after starting the operation to inspect the inside of the azeotropic separation column, a large amount of the polymer was produced therein.

Thus, it was found that the polymer was generated, that is, the manganese acetate aqueous solution itself was easily polymerized when a mother liquor containing acrylic acid by a concentration of 65% by mass was used to obtain a manganese acetate aqueous solution and the solution was fed. The pH and the like of the manganese acetate aqueous solution are collectively shown in Table 1.

Example 2

The acrylic acid was azeotropicly distilled in a similar manner to Example 1 except that a 7% by mass-acrylic acid aqueous solution produced by mixing 93 parts by mass of water and 7 parts by mass of product acrylic acid was used as a mother liquor, and manganese acetate was dissolved into the mother liquor so that the manganese acetate concentration became 25% by mass.

When continuous operation was performed under the condition for two months, a stable state was constantly obtained. As a result of inspecting the inside of the distillation column after stopping the operation, generation of a polymer was scarcely confirmed but yet the precipitation regarded as a polymer was generated in small amounts in the liquid feed pump line exclusive to the manganese acetate aqueous solution. The pH and the like of the manganese acetate aqueous solution are collectively shown in Table 1.

Example 3

The acrylic acid was azeotropicly distilled in a similar manner to Example 1 except that manganese acetate was dissolved so that the manganese acetate concentration became 25% by mass.

When continuous operation was performed under the condition for two months, a stable state was constantly obtained. As a result of inspecting the inside of the distillation column after stopping the operation, generation of a polymer was scarcely confirmed but yet the precipitation regarded as a polymer was generated in very small amounts in the liquid feed pump line exclusive to the manganese acetate aqueous solution. The pH and the like of the manganese acetate aqueous solution are collectively shown in Table 1.

Example 4

A 2% by mass-acrylic acid aqueous solution containing 0.09% by mass of acetic acid, 0.02% by mass of formic acid, 0.001% by mass of propionic acid, 0.02% by mass of maleic acid and 0.05% by mass of acrylic acid dimer, produced by diluting an acrylic acid aqueous solution as a raw material fluid of azeotropic distillation with water, was used as a mother liquor, and manganese acetate was dissolved into the mother liquor so that the manganese acetate concentration became 10% by mass. The acrylic acid was azeotropicly distilled in a similar manner to Example 1 except for using the manganese acetate aqueous solution.

When continuous operation was performed under the condition for two months, a stable state was constantly obtained. As a result of inspecting the inside of the distillation column after stopping the operation, generation of a polymer was scarcely confirmed. The pH and the like of the manganese acetate aqueous solution are collectively shown in Table 1.

Example 5

A 10% by mass-acetic acid aqueous solution produced by mixing 90 parts by mass of water and 10 parts by mass of acetic acid was used as a mother liquor, and manganese acetate was dissolved into the mother liquor so that the manganese acetate concentration became 10% by mass. The acrylic acid was azeotropicly distilled in a similar manner to Example 1 except for using the manganese acetate aqueous solution.

When continuous operation was performed under the condition for two months, a stable state was constantly obtained. As a result of inspecting the inside of the distillation column after stopping the operation, generation of a polymer was scarcely confirmed. The pH and the like of the manganese acetate aqueous solution are collectively shown in Table 1.

Example 6

Process waste water containing 2% by mass of acrylic acid, 10% by mass of acetic acid and 0.6% by mass of formic acid was used as a mother liquor, and manganese acetate was dissolved into the mother liquor so that the manganese acetate concentration became 10% by mass. The acrylic acid was azeotropicly distilled in a similar manner to Example 1 except for using the manganese acetate aqueous solution.

When continuous operation was performed under the condition for two months, a stable state was constantly obtained. As a result of inspecting the inside of the distillation column after stopping the operation, generation of a polymer was scarcely confirmed. The pH and the like of the manganese acetate aqueous solution are collectively shown in Table 1.

Comparative Example 3

A 20% by mass-acrylic acid aqueous solution produced by mixing 80 parts by mass of water and 20 parts by mass of product acrylic acid was used as a mother liquor, and manganese acetate was dissolved into the mother liquor so that the manganese acetate concentration became 10% by mass. The acrylic acid was azeotropicly distilled in a similar manner to Example 1 except for using the manganese acetate aqueous solution.

When continuous operation was performed under the above-mentioned condition for two months, plugging due to a polymer was caused during the operation in the liquid feed pump line exclusive to the manganese acetate aqueous solution to result in a state where the predetermined amount of the manganese acetate aqueous solution could not be fed. The operation was stopped 56 days after starting the operation to inspect the inside of the distillation column, and consequently, a large amount of the polymer was produced therein. The pH and the like of the manganese acetate aqueous solution are collectively shown in Table 1.

Example 7

The acrylic acid-containing gas was absorbed in accordance with the method of Example 1 in Japanese publication of unexamined patent application No. 2005-15478.

Specifically, an acrylic acid-containing gas obtained by catalytic gas phase oxidation reaction of propylene was cooled to 200° C. by a precooler and thereafter provided into an acrylic acid absorption column to obtain an acrylic acid-containing fluid. The absorption column was a packed column packed with structured packing, which had the calculated theoretical tray number of 21 and was provided with a feed opening for the acrylic acid-containing gas and an extraction opening for an absorption fluid at the bottom, with an inlet for an absorption aqueous solution and an outlet for the gas at the overhead, with a feed pipe for an overhead fluid from a distillation column at the side which is the nineteenth theoretical tray, and with a cooler for cooling a part of the gas discharged from the overhead.

Hydroquinone and a manganese acetate aqueous solution were used as polymerization inhibitors of the absorption column. With regard to hydroquinone, water containing hydroquinone equivalent to 50 ppm by mass with respect to the acrylic acid amount in the acrylic acid-containing gas provided into the absorption column was provided from the overhead. With regard to manganese acetate, a 2% by mass-acrylic acid aqueous solution produced by mixing 98 parts by mass of water and 2 parts by mass of product acrylic acid was used as a mother liquor, and manganese acetate was dissolved into the mother liquor so that the manganese acetate concentration became 10% by mass, and the solution was provided from the overhead of the absorption column. The pH of the 2% by mass-acrylic acid aqueous solution was 2.4.

The overhead temperature of the acrylic acid absorption column, the overhead pressure, the cooling temperature of a recycle gas and the recycling rate were respectively adjusted to 66.9° C., 0.11 MPa (absolute pressure), 40.6° C. and 29.0%. The whole amount of the condensate liquid obtained by the cooling of the recycle gas was circulated to the absorption column.

From the side, the circulated fluid composed of a distillatory fluid and a residual mother liquor of the distillation column, having the composition of 74.8% by mass of acrylic acid, 8.6% by mass of water, 5.1% by mass of acetic acid, 2.1% by mass of maleic acid, 0.2% by mass of furfural, 0.8% by mass of benzaldehyde, 0.2% by mass of formaldehyde, 4.2% by mass of acrylic acid dimer and 4.0% by mass of other impurities, was fed at 1.90 kg/hour. The absorption efficiency of acrylic acid in the absorption column at this time was 98.22%.

In addition, the acrylic acid-containing fluid was fed to the upper part of an acrolein separation column as a packed column having an inside diameter of 100 mm and a fill height of 5 m to separate acrolein by distillation while adjusting the overhead pressure as 265 hPa (absolute pressure) and heating so that the bottom temperature was 70° C. Thus, the acrylic acid-containing fluid, containing 89.0% by mass of acrylic acid, 3.2% by mass of water, 1.9% by mass of acetic acid, 1.1% by mass of maleic acid, 0.07% by mass of furfural, 0.3% by mass of benzaldehyde, 0.06% by mass of formaldehyde, 2.3% by mass of acrylic acid dimer and 2.07% by mass of other impurities, was obtained from the bottom at 5.10 kg/hour. This acrylic acid-containing fluid was fed to a crystallizer and crystallized to obtain product acrylic acid.

When continuous operation was performed under the condition for three months, a stable state was constantly obtained. As a result of inspecting the inside of the absorption column after stopping the operation, generation of a polymer was scarcely confirmed. Also, a stable state was constantly obtained in the continuous operation of the acrolein separation column and the crystallizer.

Further, no precipitate derived from manganese acetate was generated in the liquid feed pump line, and a trouble such as plugging was not caused.

Comparative Example 4

The acrylic acid was produced in a similar manner to Example 7 except that manganese acetate was dissolved in water to provide a manganese acetate aqueous solution having a concentration of 10% by mass into the absorption column.

When continuous operation was performed under the above-mentioned condition, plugging due to the precipitate was caused in the liquid feed pump line exclusive to the manganese acetate aqueous solution to result in a state where the predetermined amount of the manganese acetate aqueous solution could not be fed. When the operation was stopped 62 days after starting the operation to inspect the inside of the absorption column, a large amount of a polymer was produced therein.

Example 8

The acrylic acid was absorbed in a similar manner to Example 7 except that the circulated fluid composed of a distillatory fluid and a residual mother liquor of the distillation column, having the composition of 83.5% by mass of acrylic acid, 6.7% by mass of water, 3.1% by mass of acetic acid, 1.3% by mass of maleic acid, 1.4% by mass of furfural, 0.5% by mass of benzaldehyde, 0.2% by mass of formaldehyde, 2.6% by mass of acrylic acid dimer and 0.7% by mass of other impurities, was fed from the side. The acrylic acid aqueous solution, containing 90.2% by mass of acrylic acid, 3.4% by mass of water, 1.6% by mass of acetic acid, 1.0% by mass of maleic acid, 0.7% by mass of furfural, 0.3% by mass of benzaldehyde, 0.09% by mass of formaldehyde, 2.4% by mass of acrylic acid dimer and 0.31% by mass of other impurities, was obtained from the bottom of the absorption column at 6.36 kg/hour. The gas obtained from the overhead was fed to the lower part of the acrylic acid absorption column. The absorption efficiency of the acrylic acid in the absorption column at this time was 98.20%.

This acrylic acid aqueous solution was fed to a crystallizer and crystallized to obtain product acrylic acid.

When continuous operation was performed under the condition for three months, a stable state was constantly obtained. As a result of inspecting the inside of the absorption column after stopping the operation, generation of a polymer was scarcely confirmed. Also, a stable state was constantly obtained in the continuous operation of the crystallizer.

Further, no precipitation resulting from manganese acetate was caused in the liquid feed pump line, and a trouble such as plugging was not caused.

The above-mentioned results are collectively shown in Table 1. However, Examples 7 and 8 and Comparative Example 4 are not shown in Table 1.

TABLE 1

|  | Mother liquor | | | Manganese acetate aqueous solution | | | | Generation of polymer |
| --- | --- | --- | --- | --- | --- | --- | --- | --- |
|  | Kind of acid | Concentration of acid (wt %) | pH | Concentration (wt %) | Operating time | Precipitation in pipe | | in azeotropic separation column |
| Example 1 | Acrylic acid | 2 | 2.4 | 10 | 2 months | None | | Almost none |
| Example 2 | Acrylic acid | 7 | 2.3 | 25 | 2 months | Small amount was observed (b) | | Almost none |

TABLE 1-continued

|  | Mother liquor | | Manganese acetate aqueous solution | | | Precipitation in pipe | Generation of polymer in azeotropic separation column |
|---|---|---|---|---|---|---|---|
|  | Kind of acid | Concentration of acid (wt %) | pH | Concentration (wt %) | Operating time | | |
| Example 3 | Acrylic acid | 2 | 2.4 | 25 | 2 months | Very small amount was observed (b) | Almost none |
| Example 4 | Mixed acid A | 2 | 2.4 | 10 | 2 months | None | Almost none |
| Example 5 | Acetic acid | 10 | 2.3 | 10 | 2 months | None | Almost none |
| Example 6 | Mixed acid B | 12.6 | 2.3 | 10 | 2 months | None | Almost none |
| Comparative Example 1 | — | — | 7 | 10 | 48 days | Observed (a) | Large amount |
| Comparative Example 2 | Acrylic acid | 65 | 2.2 | 10 | 32 days | Observed (b) | Large amount |
| Comparative Example 3 | Acrylic acid | 20 | 2.2 | 10 | 56 days | Observed (b) | Large amount |

(A): acetic acid 0.09 wt %, formic acid 0.02 wt %, propionic acid 0.001 wt %, maleic acid 0.02 wt %, acrylic acid dimer 0.05 wt %
(B): acrylic acid 2 wt %, acetic acid 10 wt %, formic acid 0.6 wt %
(a): precipitate derived from manganese acetate
(b): precipitation of polymer As described in the results shown in Table 1, in the case where the manganese acetate aqueous solution containing no acid was fed as a polymerization inhibitor to the azeotropic separation column (Comparative Example 1), the precipitate derived from manganese acetate was generated in the pipe and the pipe was plugged. As a result, the feed amount of manganese acetate was decreased to generate a large amount of a polymer in the azeotropic separation column. Also, in the case of using the manganese acetate aqueous solution containing a comparatively large amount of acrylic acid (Comparative Examples 2 and 3), a polymer of acrylic acid was generated in the pipe, and similarly a large amount of a polymer was generated in the azeotropic separation column.

On the other hand, in Examples of the present invention, in which manganese acetate was dissolved in a mother liquor containing a proper amount of acrylic acid, a mother liquor containing an organic acid other than acrylic acid and a mother liquor containing both of these acids, and the manganese acetate aqueous solution was used as a polymerization inhibitor, the precipitate derived from manganese acetate and the generation of an acrylic acid polymer in the pipe were not observed or confirmed only in small amounts, and it was possible to operate the azeotropic separation column over two months without any generation of the polymer.

In addition, according to the comparison of Examples 2 and 3 with other Examples, it was found that the acrylic acid concentration in the manganese acetate aqueous solution is more preferably not more than 5% by mass and the manganese acetate concentration is more preferably not more than 20% by mass. By the result of Example 6, it was revealed that an organic acid other than acrylic acid gives favorable results even though the concentration in the manganese acetate aqueous solution exceeds 10% by mass.

The invention claimed is:

1. A method for producing (meth)acrylic acid, comprising steps of:
    producing a (meth)acrylic acid-containing gas by catalytic gas phase oxidation reaction; and
    obtaining a (meth)acrylic acid-containing fluid by providing the (meth)acrylic acid-containing gas into a condensation column or an absorption column;
    wherein manganese acetate is used as a polymerization inhibitor;
    manganese acetate is dissolved into
    (a) a (meth)acrylic acid aqueous solution containing not less than 0.1% by mass and not more than 7% by mass of (meth)acrylic acid, or
    (c) a mixed aqueous solution containing not less than 0.1% by mass and not more than 7% by mass of (meth)acrylic acid and an other organic acid,
    to obtain a manganese acetate aqueous solution; and
    the manganese acetate aqueous solution is provided into the condensation column or the absorption column.

2. A method for producing (meth)acrylic acid, comprising steps of:
    producing a (meth)acrylic acid-containing gas by catalytic gas phase oxidation reaction;
    obtaining a (meth)acrylic acid-containing fluid by providing the (meth)acrylic acid-containing gas into a condensation column or an absorption column; and
    purifying (meth)acrylic acid by providing the (meth)acrylic acid-containing fluid into a distillation column and/or a crystallizer;
    wherein manganese acetate is used as a polymerization inhibitor;
    manganese acetate is dissolved into
    (a) a (meth)acrylic acid aqueous solution containing not less than 0.1% by mass and not more than 7% by mass of (meth)acrylic acid, or
    (c) a mixed aqueous solution containing not less than 0.1% by mass and not more than 7% by mass of (meth)acrylic acid and an other organic acid, to obtain a manganese acetate aqueous solution; and
    the manganese acetate aqueous solution is provided into one or more selected from a group consisting of the condensation column, the absorption column and the distillation column.

3. A method for producing (meth)acrylic acid, comprising steps of:
    producing a (meth)acrylic acid-containing gas by catalytic gas phase oxidation reaction;
    obtaining a (meth)acrylic acid-containing fluid by providing the (meth)acrylic acid-containing gas into an absorption column; and
    purifying (meth)acrylic acid by providing the (meth)acrylic acid-containing fluid into an azeotropic separation column and azeotropicly distilling the (meth)acrylic acid-containing fluid in the presence of an azeotropic agent;

wherein manganese acetate is used as a polymerization inhibitor;

manganese acetate is dissolved into (a) a (meth)acrylic acid aqueous solution containing not less than 0.1% by mass and not more than 7% by mass of (meth)acrylic acid, or (c) a mixed aqueous solution containing not less than 0.1% by mass and not more than 7% by mass of (meth)acrylic acid and an other organic acid, to obtain a manganese acetate aqueous solution; and the manganese acetate aqueous solution is provided into the absorption column and/or the azeotropic separation column.

4. The method for producing (meth)acrylic acid according to claim 1, wherein one or more selected from a group consisting of formic acid, acetic acid, propionic acid, maleic acid and (meth)acrylic acid dimer is used as the other organic acid.

5. The method for producing (meth)acrylic acid according to claim 2, wherein one or more selected from a group consisting of formic acid, acetic acid, propionic acid, maleic acid and (meth)acrylic acid dimer is used as the other organic acid.

6. The method for producing (meth)acrylic acid according to claim 3, wherein one or more selected from a group consisting of formic acid, acetic acid, propionic acid, maleic acid and (meth)acrylic acid dimer is used as the other organic acid.

7. The method for producing (meth)acrylic acid according to claim 1, wherein a concentration of manganese acetate in the manganese acetate aqueous solution is not less than 0.1% by mass and not more than 20% by mass.

8. The method for producing (meth)acrylic acid according to claim 2, wherein a concentration of manganese acetate in the manganese acetate aqueous solution is not less than 0.1% by mass and not more than 20% by mass.

9. The method for producing (meth)acrylic acid according to claim 3, wherein a concentration of manganese acetate in the manganese acetate aqueous solution is not less than 0.1% by mass and not more than 20% by mass.

10. The method for producing (meth)acrylic acid according to claim 1, wherein the concentration of (meth)acrylic acid in (a) and (c) is not more than 5% by mass.

11. The method for producing (meth)acrylic acid according to claim 2, wherein the concentration of (meth)acrylic acid in (a) and (c) is not more than 5% by mass.

12. The method for producing (meth)acrylic acid according to claim 3, wherein the concentration of (meth)acrylic acid in (a) and (c) is not more than 5% by mass.

13. The method for producing (meth)acrylic acid according to claim 1, wherein the (meth)acrylic acid aqueous solution of (a) is (1) a (meth)acrylic acid aqueous solution wherein concentration is adjusted by adding water to crude (meth)acrylic acid or purified (meth)acrylic acid obtained through a purification process; or (2) a (meth)acrylic acid aqueous solution wherein concentration is adjusted by adding water to a (meth)acrylic acid solution obtained from the condensation column or the absorption column.

14. The method for producing (meth)acrylic acid according to claim 2, wherein the (meth)acrylic acid aqueous solution of (a) is (1) a (meth)acrylic acid aqueous solution wherein concentration is adjusted by adding water to crude (meth)acrylic acid or purified (meth)acrylic acid obtained through a purification process; or (2) a (meth)acrylic acid aqueous solution wherein concentration is adjusted by adding water to (meth)acrylic acid solution obtained from the condensation column or the absorption column.

15. The method for producing (meth)acrylic acid according to claim 3, wherein the (meth)acrylic acid aqueous solution of (a) is (1) a (meth)acrylic acid aqueous solution wherein concentration is adjusted by adding water to crude (meth)acrylic acid or purified (meth)acrylic acid obtained through a purification process; or (2) a (meth)acrylic acid aqueous solution wherein concentration is adjusted by adding water to (meth)acrylic acid solution obtained from the condensation column or the absorption column.

16. The method for producing (meth)acrylic acid according to claim 1, wherein the mixed aqueous solution of (c) is an aqueous solution wherein concentration is adjusted by adding water to a process waste water containing (meth)acrylic acid, formic acid, acetic acid, propionic acid, maleic acid or (meth)acrylic acid dimer, obtained in the process for producing (meth)acrylic acid.

17. The method for producing (meth)acrylic acid according to claim 2, wherein the mixed aqueous solution of (c) is an aqueous solution wherein concentration is adjusted by adding water to a process waste water containing (meth)acrylic acid, formic acid, acetic acid, propionic acid, maleic acid or (meth)acrylic acid dimer, obtained in the process for producing (meth)acrylic acid.

18. The method for producing (meth)acrylic acid according to claim 3, wherein the mixed aqueous solution of (c) is an aqueous solution wherein concentration is adjusted by adding water to a process waste water containing (meth)acrylic acid, formic acid, acetic acid, propionic acid, maleic acid or (meth)acrylic acid dimer, obtained in the process for producing (meth)acrylic acid.

* * * * *